United States Patent [19]

Ono et al.

[11] Patent Number: 4,654,445

[45] Date of Patent: Mar. 31, 1987

[54] PREPARATION PROCESS OF 2-CHLOROPROPIONALDEHYDE

[75] Inventors: Hiroshi Ono, Fujisawa; Kanemitsu Miyama, Mobara; Takaharu Kasuga, Kamakura, all of Japan

[73] Assignee: Mitsui Toatsu Chemicals Incorporated, Tokyo, Japan

[21] Appl. No.: 800,966

[22] Filed: Nov. 22, 1985

[30] Foreign Application Priority Data

| Nov. 26, 1984 | [JP] | Japan | 59-248196 |
| Jul. 9, 1985 | [JP] | Japan | 60-149169 |
| Jul. 22, 1985 | [JP] | Japan | 60-160364 |
| Oct. 24, 1985 | [JP] | Japan | 60-236412 |

[51] Int. Cl.$^4$ ............................................. C07C 45/50
[52] U.S. Cl. ..................................... 568/454; 568/455
[58] Field of Search ................................ 568/454, 455

[56] References Cited

U.S. PATENT DOCUMENTS

| 3,239,570 | 3/1966 | Slaugh et al. | 568/454 |
| 4,045,492 | 8/1977 | Kniese et al. | 568/454 |
| 4,370,504 | 1/1983 | Ojima et al. | 568/454 |
| 4,496,769 | 1/1985 | Denise et al. | 568/454 |

FOREIGN PATENT DOCUMENTS

| 725670 | 1/1966 | Canada | 568/454 |
| 1397779 | 3/1965 | France | 568/454 |
| 1448255 | 9/1976 | United Kingdom | 568/455 |

OTHER PUBLICATIONS

Helvetica Chimica Acta, 48(5) 1151–1157, 1965.
Tetrahedron Letters No. 22, 1725–1726, 1969.

*Primary Examiner*—Werren B. Lone
*Attorney, Agent, or Firm*—Cushman, Darby & Cushman

[57] ABSTRACT

This invention relates to a process for preparing 2-chloropropionaldehyde (2-CPA) by using vinyl chloride, carbon monoxide and hydrogen as raw materials. Although processes making use of cobalt catalysts have conventionally been known, it is disclosed herein that by using a rhodium compound and a nitrogen- or phosphorus-containing Lewis base in combination as a catalyst, the reaction is allowed to proceed at temperature and pressure lower than those required for such conventional processes and the selectively toward the intended product is improved. It is also disclosed that by causing water to exist in the reaction system and using a water-insoluble organic solvent, fractionating the reaction mixture into a water layer and an organic layer after the reaction and then collecting 2-CPA from the water layer through distillation, extraction or the like, the rhodium compound contained substantially in its entirety in an organic layer can be reutilized in the form of its solution. This process is an extremely good process suitable for use in the preparation of 2-CPA which is useful as an intermediate for chemical products, agricultural chemicals, pharmaceutical products, etc.

12 Claims, No Drawings

PREPARATION PROCESS OF 2-CHLOROPROPIONALDEHYDE

BACKGROUND OF THE INVENTION (1) Field of the Invention

This invention relates to a process for preparing 2-chloropropionaldehyde from vinyl chloride, carbon monoxide and hydrogen as raw materials in accordance with the following reaction formula (1):

$$CH_2=CHCl + CO + H_2 \rightarrow CH_3\text{-}CHCl\text{-}CHO \qquad (1)$$

2-Chloropropionaldehyde is useful as an intermediate for chemical products, agricultural chemicals, pharmaceutical products, etc.

(2) Description of the Prior Art

It has been known to prepare 2-chloropropionaldehyde from vinyl chloride, carbon monoxide and hydrogen as raw materials, as disclosed by way of example in French Patent No. 1,397,779 and HELVETICA CHIMICA ACTA, 48(5), 1151-1157. All of these processes employ cobalt carbonyl as a catalyst. In French Patent No. 1,397,779 referred to above by way of example, the raw materials were reacted for 90 minutes under conditions of a reaction temperature of 110° C. and a reaction pressure of 200 atm, whereby such productivity as a vinyl chloride conversion of 57.4% and a selectivity of 86.2% toward 2-chloropropionaldehyde was obtained.

However, these conventional processes which employ cobalt carbonyl as a catalyst require cobalt carbonyl in a large amount and a reaction pressure as high as 160-200 atm because the catalytic activity of cobalt is extremely low. Moreover, the reaction is caused to proceed at a reaction temperature of 75°–125° C. for 90–120 minutes. The intended product, 2-chloropropionaldehyde, is a thermally-unstable material. Under the conditions of such a reaction temperature and reaction time, a substantial portion of 2-chloropropionaldehyde is consumed through a consecutive reaction and the reaction yield is thus reduced. Accordingly, these processes have poor reproducibility. Furthermore, hydrogen chloride is byproduced through this consecutive reaction or other side reactions. The byproduction of hydrogen chloride has raised such problems that it causes materials of each reactor to undergo severe corrosion and it reacts with the catalyst, cobalt carbonyl, into cobalt chloride, thereby developing an obstacle to the reutilization of the catalyst.

Some attempts have also been made to apply rhodium catalysts, which have generally been known to exhibit higher activities than cobalt catalysts in oxo reactions, to the above reaction. None of such attempts have however yet proved successful. Reference may for example be made to Tetrahedron Letters, 1969, 22, 1725–1726, in which G. Wilkinson et al conducted the hydroformylation of various unsaturated compounds by using carbonylhydridotris(triphenylphosphine)rhodium [RhH(CO)(PPh$_3$)$_3$] as a catalyst. In the case of vinyl chloride, they reported occurrence of RhCl(CO)(PPh$_3$)$_2$ and alkenes only. The above attempts are however absolutely silent about such a process that 2-chloropropionaldehyde, the reaction product, and its catalytic component are separated to obtain 2-chloropropionaldehyde with a good yield and at the same time to permit reutilization of the catalyst. As already described above, the reaction product, 2-chloropropionaldehyde, is thermally unstable and the rhodium compound, the catalyst component, also includes some facets for which the rhodium compound may not be said sufficiently stable to heat. For these reasons, the yield of 2-chloropropionaldehyde may not be raised to any sufficient level if its recovery is effected by mere distillation of the reaction mixture. In some instances, it may also be observed that the rhodium catalyst separated and recovered by such a method does not show sufficient activity With the foregoing in view, there has been a long-standing demand for the development of a method for the efficient separation of the reaction product and catalyst.

SUMMARY OF THE INVENTION

The first object of this invention is to provide an improved process for the preparation of 2-chloropropionaldehyde from vinyl chloride, carbon monoxide and hydrogen as raw materials.

The second object of this invention is to provide a novel catalyst which permits synthesis of 2-chloropropionaldehyde with higher activity and selectivity under reaction conditions milder compared with the conventional art.

The third object of this invention is to provide a method in which upon preparation of 2-chloropropionaldehyde with such a catalyst, the reaction product, i.e., 2-chloropropionaldehyde is collected with good efficiency from a reaction mixture of 2-chloropropionaldehyde and the rhodium compound as the catalyst and the rhodium compound is recovered in a reusable form and is recycled to the reaction system for its reutilization.

The first and second objects of this invention have been achieved by finding that when vinyl chloride, carbon monoxide and hydrogen are reacted in the presence of a catalyst composed in combination of a rhodium compound and a specific base, the reaction proceeds at temperature and pressure lower than those required for conventional cobalt catalysts and sufficient selectivity toward the intended product can also be obtained; and the productivity is improved further if the above reaction is carried out in the presence of water.

The third object of this invention has also been fulfilled by finding that if an organic solvent either insoluble or hardly soluble in water is employed and water is allowed to exist in a suitable amount in the above process and the organic layer and water layer are fractionated subsequent to the reaction, the majority of 2-chloropropionaldehyde is contained in the water layer and is readily separated from water by its distillation under reduced pressure, and the rhodium catalyst is contained substantially in its entirety in the organic layer and is reusable by recycling the organic layer to the reaction system.

The term "specific base" as used herein means a Lewis base containing a Group-VB element of the periodic table such as nitrogen, phosphorus or arsenic. As a particularly preferred base, may be mentioned a combination of a compound represented by the following general formula:

$$P(R^1R^2R^3)$$

wherein P means a phosphorus atom, and $R^1$, $R^2$ and $R^3$ denote individually an alkyl, aryl, cycloalkyl, alkoxy, aryloxy or cycloalkoxy group, and a nitrogen-containing compound the pKa of which is in the range of 4–10.

DETAILED DESCRIPTION OF THE INVENTION

The process of this invention features to conduct the reaction of vinyl chloride, carbon monoxide and hydrogen in the presence of a catalyst composed of a rhodium compound and a base upon synthesizing 2-chloropropionaldehyde from such reactants as raw materials.

The term "base" as used herein means a Lewis base containing a Group-VB element of the periodic table such as nitrogen, phosphorus or arsenic. The rhodium compound does not show any catalytic effect to the present reaction in the absence of such a base. Even if water is not present, the reaction is still allowed to proceed with rather good productivity so long as such a base is caused to exist. Existence of water can improve the productivity of the reaction further to such a degree that can be hardly reached by a mere combination of a rhodium compound and a base.

The process of this invention will hereinafter be described in further detail.

As mentioned above, the term "base" as used herein means a Lewis base containing a Group-VB element of the periodic table such as nitrogen, phosphorus or arsenic. Among such bases, preferred bases are compounds represented individually by the following general formula:

wherein P means a phosphorus atom, and $R^1$, $R^2$ and $R^3$ denote individually an alkyl, aryl, cycloalkyl, alkoxy, aryloxy or cycloalkoxy group as well as nitrogen-containing compounds each of which has a pKa in the range of 4–10. Especially, it is more preferable that the base is composed in combination of at least one compound represented by the above general formula $P(R^1R^2R^3)$ and at least one nitrogen-containing compound the pKa of which is in the range of 4–10.

As compounds represented by the general formula $P(R^1R^2R^3)$, may be mentioned phosphines such as trimethylphosphine, triethylphosphine, tripropylphosphine, tributylphosphine, trioctylphosphine, triphenylphosphine, tricyclohexylphosphine and tribenzylphosphine; phosphites such as trimethylphosphite, triethylphosphite, tripropylphosphite, tributylphosphite, trioctylphosphite, triphenylphosphite, tricyclohexylphosphite and tribenzylphosphite; etc. As a base, bis(1,2-diphenylphosphino)ethane may be used.

On the other hand, illustrative of the nitrogen-containing compound the pKa of which is in the range of 4–10 may generally include amino-containing compounds, for example, aliphatic amines, aromatic amines, diamines, triamines, amino alcohols, amino acids, amides, urea compounds, guanidines and amidines as well as nitrogen-containing compounds formed by bonding substituent groups such as alkyl groups, aryl groups, carboxyl group, hydroxyl group and/or halogen atoms to the nitrogen atoms, carbon atoms and/or the like of the above compounds, the pKa of each of which falls in the range of 4–10.

Besides, among heterocyclic compounds each of which contains one or more nitrogen atoms, compounds pKa of each of which ranges from 4 to 10 may be used preferably. As examples of these compounds, pyridine compounds, quinoline compounds, imidazole compounds, piperazine compounds, morpholine compounds and thiazole compounds, the pKa of each of which is in the range of 4–10, may be used preferably.

Among these nitrogen-containing compounds the pKa of each of which ranges from 4 to 10, nitrogen-containing compounds having pKa levels in the range of 4–10 and selected from pyridine compounds, quinoline compounds, imidazole compounds and morpholine compounds are particularly preferred. As specific examples of these particularly preferable compounds, may be mentioned as pyridine compounds those represented by the following general formula:

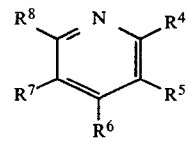

wherein $R^4$, $R^5$, $R^6$, $R^7$ and $R^8$ are individually a hydrogen or halogen atom or an alkyl, aryl, cycloalkyl, hydroxyl, alkoxy, aryloxy, cycloalkoxy, carboxyl or acetyl group and having pKa levels in the range of 4–10. Illustrative of such pyridine compounds may include pyridine, picoline, ethylpyridine, 2,4-lutidine, α-collidine, phenylpyridine, cyclohexylpyridine, benzylpyridine, 3-piridinol, methoxypyridine, phenoxypyridine, aminopyridine and the like. Besides, polynuclear pyridines such as 2,2'-bispyridine may also be mentioned as other exemplary pyridine compounds.

On the other hand, illustrative of quinoline compounds may include, besides quinoline, 2-methylquinoline, 4-methylquinoline, dimethylquinoline, 2-ethylquinoline, phenylquinoline, methoxyquinoline and so on. In addition, various isoquinoline compounds may also be used.

Illustrative imidazole compounds may be those represented by the following general formula:

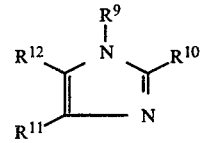

wherein $R^9$, $R^{10}$, $R^{11}$ and $R^{12}$ mean individually a hydrogen atom or an alkyl, aryl or cycloalkyl group, and $R^{11}$ and $R^{12}$ may optionally form a ring together with the 4-position and 5-position carbon atoms to form an imidazole compound with a condensed ring, and having pKa levels in the range of 4–10. As examples of such imidazole compounds, may be mentioned imidazole, N-methylimidazole, N-ethylimidazole, 2-methylimidazole, 2-ethyl-4-methylimidazole, 2-phenylimidazole, 2-undecylimidazole, N-benzyl-2-methylimidazole, 2,4,5-triphenylimidazole, benzimidazole, 2-methylbenzimidazole, 2-phenylbenzimidazole, etc. Exemplary morpholine compounds may include N-methylmorpholine, N-ethylmorpholine and the like in addition to morpholine.

As rhodium compounds useful in the practice of the process of this invention, there are the oxide, mineral acid salts and organic acid salts of rhodium as well as rhodium complex compounds. Among a variety of these rhodium compounds, rhodium compounds free of any halogen are particularly preferred. As examples of such rhodium compounds, may be mentioned rhodium oxide, rhodium nitrate, rhodium sulfate, rhodium acetate, rhodium(III)acetylacetonate, dicarbonylacetylacetonato rhodium, dodecacarbonyl tetrarhodium, hexadecacarbonyl hexarhodium and the like. As a method for forming a halogen-free rhodium compound in a reaction system, it is possible to use a halogen-containing rhodium compound such as rhodium chloride, rhodium bromide, rhodium iodide or dichlorotetracarbonyldirhodium and then to add an alkaline compound, for example, sodium hydroxide, potassium hydroxide, potassium carbonate, trimethylamine, triethylamine or the like in an amount equivalent to the halogen atoms of the rhodium compound to the reaction system. The above-mentioned base and rhodium compound which may preferably be used in the process of this invention may be used more preferably in the form of a complex compound of the rhodium compound and at least part of the base. As exemplary complex compounds, may be mentioned carbonylhydridotris(triphenylphosphine)rhodium [RhH(CO)(Ph$_3$P)$_3$], nitrosyltris(triphenylphosphine)rhodium [Rh(NO)(Ph$_3$P)$_3$], $\eta$-cyclopentadienylbis(triphenylphosphine)rhodium [Rh(C$_5$H$_5$)(Ph$_3$P)$_2$], etc.

Although the process of this invention may be practiced in a liquid phase containing these rhodium compound, base, water and vinyl chloride without any particular need for another solvent, it may also be carried out in the presence of a solvent. As solvents for reactions, it is generally possible to use saturated hydrocarbons such as heptane, hexane, octane, decane, dodecane and the like, aromatic hydrocarbons such as benzene, toluene, xylene and the like, halogenated hydrocarbons such as monochlorobenzene, orthodichlorobenzene and parachlorotoluene, alcohols such as methanol, ethanol, propanol, butanol, pentanol, octanol and the like, esters such as butyl acetate, $\gamma$-butyrolactone and the like, ethers such as tetrahydrofuran, ethylene glycol dimethyl ether, diglime, tetraglime and the like, ketones such as acetone, methyl isobutyl ketone and the like, aldehydes such as propionaldehyde, butylaldehyde and the like, acid anhydrides such as acetic anhydride and the like, nitriles such as acetonitrile, propionitrile and the like, amides such as N-methylpyrrolidone and the like, ureas such as dimethylimidazolidinone, tetramethylurea, etc., carbonate esters such as ethylene carbonate, propylene carbonate and the like, and so on.

In the process of this invention, no particular limitation is imposed on the amount of water to be existed during the reaction. However, its effect is limited if incorporated in an extremely small amount. Generally, the amount of water is sufficient if it is 0.0001 or more in terms of its weight ratio to vinyl chloride to be supplied as a raw material to each reactor. Similarly, no particular limitation is imposed on the upper limit of the amount of water to be employed. In view of the productivity of the intended product per volume of the reactor, it is suitable to use water in an weight ratio of 1,000 or less relative to vinyl chloride to be fed as a raw material to the reactor. A range of 0.001–100 is particularly preferred because the effect of water is remarkable within that range. The supply of water may be effected in its liquid form. However, in some instances, water may be fed in the form of steam together with one or more feed gases to a reactor. Alternatively, water may also be fed in the form of liquid dissolved in a solvent which is used for the reaction.

In the process of this invention, the above-described rhodium compound may be used in an amount of $10^{-4}$–$10^3$ milligram atoms or preferably 0.1–50 milligram atoms in terms of as rhodium atoms per mole of vinyl chloride to be fed as a raw material. On the other hand, the base may be used in an amount of 0.1–500 moles or preferably 0.5–100 moles per gram atom of rhodium.

The process of this invention is usually carried out at a reaction temperature of 20°–150° C. and at a reaction pressure of 10–200 kg/cm$^2$G or preferably 30–150 kg/cm$^2$G. The lower the reaction temperature, the better in view of the low thermal stability of resulting 2-chloropropionaldehyde. For this reason, 20°–100° C. is a particularly preferred temperature range. The mixing molar ratio of carbon monoxide and hydrogen, both of which are used as raw materials, may generally within the range of 10–0.1 or preferably 4–0.2. Carbon monoxide and hydrogen may thus be provided as a mixed gas which contains both components at the aforementioned composition ratio. Water gas may thus be used either as is or in combination with a gas inert to the reaction such as methane or nitrogen or with carbon dioxide. The other raw material, namely, vinyl chloride may be used in its gaseous or liquid form or in the form of a solution dissolved in a solvent which is used for the reaction.

The process of this invention may be practiced in accordance with any one of the batch, semi-batch or continuous process. In the case of the batch process for example, vinyl chloride is added in its gaseous or liquid form or as a solution to an autoclave in which a catalyst, water and optionally a solvent have been charged. A gas containing carbon monoxide and hydrogen is then introduced in the autoclave to a predetermined pressure. By heating the autoclave, the reaction is allowed to proceed. In the case of the continuous process, a liquid consisting of a catalyst, water, vinyl chloride and optionally a solvent and a gas containing carbon monoxide and hydrogen are continuously introduced into a pressure-resistant reactor at a location thereof while a liquid consisting of the reaction product, the catalyst, water, unreacted vinyl chloride and optionally the solvent and unreacted carbon dioxide and hydrogen are continuously taken out of the reactor at another location thereof. Vinyl chloride may be introduced in its gaseous form together with a mixed gas of carbon monoxide and hydrogen, which are raw materials, into the reaction vessel. As a modification of the continuous process, a catalyst and optionally a solvent are charged in advance in a reactor. Then, water and the raw materials, namely, vinyl chloride, carbon monoxide and hydrogen are continuously introduced into the reactor at a lower location thereof while water, unreacted vinyl chloride, carbon monoxide, hydrogen and the reaction product are continuously taken out of the reactor at an upper location thereof.

When vinyl chloride, carbon monoxide and hydrogen are reacted in the presence of a rhodium compound, a base, an organic solvent either insoluble or hardly soluble in water and water; the thus-obtained reaction mixture is fractionated into a water layer and an organic layer; the organic layer, which contains the rhodium compound, is recycled to the reaction system for the reutilization of the rhodium compound; and in the meantime, 2-chloropropionaldehyde is recovered from the water layer, in which the 2-chloropropionaldehyde is contained, by distillation, extraction or the like, the solvent and water may be used in amounts different from those given above as preferred ranges by way of example and the reaction may be effected in a manner different from the reaction methods also given above by way of example. Namely, the solvent employed for the above reaction is required to be an organic solvent which is either insoluble or hardly soluble in water.

The term "organic solvent which is either insoluble or hardly soluble in water" as used herein means an organic solvent which is insoluble in water or has a low degree of solubility to water. Organic solvents may generally be used so long as their solubilities in water are below 5% by volume at their application temperatures. From the industrial viewpoint, it is preferable to use an organic solvent the water-solubility of which is below 0.5% by weight. Furthermore, it is particularly preferred that these solvents are stable and inert in the reaction system.

Hydrocarbons are especially preferred as such solvents. Specifically, may preferably used saturated hydrocarbons such as hexane, heptane, octane, nonane and decane, aromatic hydrocarbons such as benzene, toluene and xylene, halogenated hydrocarbons such as monochlorobenzene, orthodichlorobenzene and parachlorotoluene, etc. Mixtures of hydrocarbons, such as ligroine, kerosene, light oil and diesel oil which are available industrially, may also be included in such preferred solvents.

Besides, ethers such as dipropyl ether and dibutyl ether, ketones such as diisobutyl ketone and phorone, esters such as butyl butyrate and butyl benzoate and the like may also be mentioned as preferred solvents.

The solubility of 2-chloropropionaldehyde in these organic solvents which are either insoluble or hardly soluble in water is not critical too much, because the water-solubility of 2-chloropropionaldehyde is extremely large. If the solubility of 2-chloropropionaldehyde in one or more of these organic solvents is so high that the reduction to the yield of the intended reaction product, i.e., 2-chloropropionaldehyde is unignorably large, it is preferable to extract any remaining 2-chloropropionaldehyde with water from an organic layer and then to recycle the organic layer for its reutilization instead of recycling the organic layer as is to the reaction system after fractionating the reaction mixture into a water layer and the organic layer. This aspect is also included in the present invention. In this procedure, it is also preferable to lower the concentration of 2-chloropropionaldehyde in the organic layer below 5 wt. % or preferably 1 wt. % by its water extraction.

In the above procedure, no particular limitation is vested on the amount of water to be allowed to exist during the reaction. However, the effect of water will be reduced when water is added in an extremely small amount. Usually, the amount of water may be 0.01 or more in terms of its weight ratio to vinyl chloride which is to be fed as a raw material to a reactor. No particular limitation is imposed on the upper limit of water to be employed. It is however suitable to add water at a weight ratio of 1,000 or smaller relative to vinyl chloride to be fed as a raw material to a reactor in view of the productivity of the intended reaction product per volume of the reactor. It is preferable to add water at a weight ratio of 0.1–100, in which range the effect of water can be brought about to a particularly remarkable extent. Water may be fed in its liquid form. In some instances, it may be used as a solution in which a base, one of the catalyst components, is dissolved. Especially when a water-soluble pyridine compound, quinoline compound, imidazole compound or morpholine compound is used as a base, such a base may be fed as an aqueous solution to the reaction system. In this case, when the resultant reaction mixture is fractionated into a water layer and an organic layer, the water layer contains a substantial portion of the base. Thus, the remaining water layer which has been obtained by recovering the reaction product, 2-chloropropionaldehyde, from the fractionated water layer takes the form of an aqueous solution with the base contained therein. From the industrial viewpoint, it is preferable to reuse the remaining water layer. When the water layer is recycled for its reutilization, byproducts which may give some unignorable deleterious effects to the reaction tend to accumulate therein through repetition of its recycled reutilization although their amounts vary depending on reaction conditions. It is hence preferable to subject at least part of the water layer to a purification step upon its reutilization so that at least parts of such byproducts are taken out of the reaction system. As a purification step for the removal of such byproducts, it may be mentioned to effect its purification with a cation-exchange resin and an anion-exchange resin or to obtain the base with a raised purity or an aqueous solution of the base from the base-containing aqueous solution by distillation, crystallization, membrane separation, adsorption, extraction or the like.

The above-described process may be practiced by either one of the batch, semi-batch and continuous processes. As one example of the batch process, vinyl chloride is added in its gaseous or liquid form or as a solution to an autoclave which has been charged with a rhodium compound, a base, an organic solvent either insoluble or hardly soluble in water and water. Then, a gas containing carbon monoxide and hydrogen is introduced into the autoclave to a predetermined pressure. By heating the contents with stirring, the reaction is allowed to proceed. The thus-obtained reaction mixture is thereafter left at rest, in other words, subjected to gravity settling so that it is separated into a water layer and an organic layer. The organic layer is again charged in the autoclave, to which water or in some instances, water and a base or an aqueous solution containing the base may be added for its reutilization. On the other hand, the water layer is subjected to distillation, extraction or the like so as to obtain 2-chloropropionaldehyde.

As one example of the continuous process, an organic solvent either insoluble or hardly soluble in water and containing a rhodium compound and a base, water or an aqueous solution containing the base, and the raw materials, i.e., vinyl chloride, carbon monoxide and hydrogen are continuously fed to a reaction vessel. The reaction vessel is preferably equipped with a stirrer. However, the stirrer may not be required depending on the manner of supply of the raw materials, namely, carbon monoxide and/or hydrogen. By maintaining the reaction vessel at a prescribed temperature and pressure, the raw materials which have been fed continuously are allowed to undergo the reaction. The thus-obtained reaction mixture is then taken out of the reaction vessel, followed by its fractionation into an organic layer and a water later through its separation at rest. The organic layer is recycled to the reaction vessel for its reutilization. At the same time, water or the base or an aqueous solution of the base is supplied to the reaction vessel. By a method similar to that employed in the above-described batch process, 2-chloropropionaldehyde is obtained from the water layer. Depending on the type of a base to be employed, an aqueous solution containing the base may be obtained as a residue at this time.

After subjecting at least part of such an aqueous solution to purification, it may be employed as an aqueous solution of the base to be fed to the reaction vessel.

EXAMPLE 1

After sweeping with nitrogen gas the interior of an autoclave which was equipped with a stirrer, had an internal volume of 50 ml and was made of stainless steel, the autoclave was charged with 184 mg (0.2 milligram atom as Rh) of carbonylhydridotris(triphenylphosphine)rhodium and 335 mg (5 millimoles) of imidazole, followed by a further addition of 20 ml of a toluene solution which contained 3.75 g (60 millimoles) of vinyl chloride. A 1:2 (by molar ratio) mixed gas of carbon monoxide and hydrogen was then charged under pressure and at room temperature into the autoclave until the interior pressure increased to 75 kg/cm$^2$G. Thereafter, the autoclave was raised to 40° C. at which the contents were reacted for 60 minutes. After cooling the autoclave down to room temperature, the unreacted mixed feed gas was collected in a gas-sampling bag and the autoclave was then opened to take out the reaction mixture containing the catalyst, solvent and reaction product. The gas and the reaction mixture were both quantitatively analyzed by gas chromatography. As a result, the conversion of vinyl chloride and the yield of 2-chloropropionaldehyde were respectively found to be 15.5% and 8.3 millimoles (selectivity: 89.2% based on the converted vinyl chloride). It was also found that propionaldehyde occurred as a principal byproduct with a selectivity of 5.1%.

EXAMPLES 2–7

Reactions were conducted in the same manner as in Example 1 except that the reaction temperature, the reaction pressure, the molar ratio of carbon monoxide to hydrogen and the reaction time were changed. Results are summarized in Table 1.

TABLE 1

| Ex. | Reaction temperature (°C.) | Reaction pressure (kg/cm G) | Molar ratio of carbon monoxide to hydrogen | Reaction time (min.) | Conversion of vinyl chloride (%) | Selectivity toward 2-chloropropionaldehyde (%) |
|---|---|---|---|---|---|---|
| 2 | 30 | 75 | 1:2 | 120 | 11.0 | 89.6 |
| 3 | 60 | 60 | 1:2 | 30 | 12.1 | 89.9 |
| 4 | 80 | 90 | 1:2 | 15 | 18.4 | 90.1 |
| 5 | 100 | 110 | 1:2 | 10 | 15.1 | 87.4 |
| 6 | 40 | 40 | 2:1 | 30 | 5.8 | 91.5 |
| 7 | 40 | 125 | 1:4 | 30 | 21.0 | 91.0 |

EXAMPLES 8–11

Reactions were effected in the same manner as in Example 1 except that carbonylhydridotris(triphenylphosphine)rhodium and imidazole were used in different amounts. Results are summarized in Table 2.

TABLE 2

| Example | Amount of added carbonylhydridotris(triphenylphosphine)rhodium (mmol) | Amount of added imidazole (mmol) | Conversion of vinyl chloride (%) | Selectivity toward 2-chloropropionaldehyde (%) |
|---|---|---|---|---|
| 8 | 0.2 | 1.0 | 6.1 | 93.9 |
| 9 | 0.2 | 10.0 | 7.3 | 88.1 |
| 10 | 0.05 | 5.0 | 2.0 | 82.0 |
| 11 | 1.5 | 1.5 | 28.3 | 79.2 |

EXAMPLES 12–22

Reactions were effected for 30 minutes in the same manner as in Example 1 except that the reaction temperature was set at 80° C. and various bases were respectively used in lieu of imidazole. Results are summarized in Table 3.

TABLE 3

| Ex. | Base | Conversion of vinyl chloride (%) | Selectivity toward 2-chloropropionaldehyde (%) |
|---|---|---|---|
| 12 | N—Methylimidazole | 12.1 | 90.1 |
| 13 | 2-Methylimidazole | 3.5 | 88.2 |
| 14 | 2-Ethyl-4-methyl-Imidazole | 3.1 | 86.3 |
| 15 | 2-Undecylimidazole | 2.8 | 82.8 |
| 16 | N—Benzyl-2-methyl-Imidazole | 2.8 | 81.6 |
| 17 | Benzimidazole | 6.4 | 83.4 |
| 18 | 2-Methylbenzimidazole | 3.7 | 82.6 |
| 19 | Triphenylphosphine | 1.5 | 88.5 |
| 20 | Tributylphosphine | 1.3 | 90.5 |
| 21 | Trimethylphosphite | 1.8 | 90.2 |
| 22 | Tricyclohexylphosphite | 1.2 | 86.3 |

EXAMPLES 23–31

Reactions were carried out in the same manner as in Example 1 except that various solvents were respectively used in place of toluene. Results are summarized in Table 4.

TABLE 4

| Ex. | Solvent | Conversion of vinyl chloride (%) | Selectivity toward 2-chloropropionaldehyde (%) |
|---|---|---|---|
| 23 | Benzene | 16.3 | 90.1 |
| 24 | o-Xylene | 14.2 | 88.6 |
| 25 | Hexane | 2.8 | 92.1 |
| 26 | Orthodichlorobenzene | 17.3 | 88.3 |
| 27 | Ethanol | 1.6 | 78.4 |
| 28 | γ-Butyrolactone | 1.3 | 81.4 |
| 29 | Diglime | 11.5 | 87.6 |
| 30 | Acetone | 6.2 | 80.3 |
| 31 | Acetonitrile | 4.2 | 71.4 |

Example 32

A reaction was carried out in the same manner as in Example 1 except that the reaction temperature was changed to 80° C. and 36 mg of hexadecacarbonyl hexarhodium and 157 mg of triphenylposphine were used in place of carbonylhydridotris(triphenylphosphine)r- hodium. From analyses of the unreacted mixed feed gas and reaction mixture, the following productivity was obtained. Conversion of vinyl chloride: 31.1%. Selectivity toward 2-chloropropionaldehyde: 87.1%.

Examples 33–37

Reactions were conducted in the same manner as in Example 32 except that in place of the combination of hexadecacarbonyl hexarhodium and triphenylphosphine, various combinations of catalysts were respectively employed. Results are summarized in Table 5.

TABLE 5

| Example | Catalyst Name of material | Amount (mg) | Conversion of vinyl chloride (%) | Selectivity toward 2-chloropropionaldehyde (%) |
|---|---|---|---|---|
| 33 | Dodecacarbonyl tetrarhodium $Rh_4(CO)_{12}$ | 37 | 29.5 | 88.4 |
| | Triphenylphosphine | 157 | | |
| 34 | Dicarbonylacetylacetonato rhodium $Rh(CO)_2(C_5H_7O_2)$ | 52 | 21.0 | 86.2 |
| | Triphenylphosphine | 157 | | |
| 35 | Hexadecacarbonyl hexarhodium $Rh_6(CO)_{16}$ | 36 | 12.0 | 83.1 |
| | Tri-n-butylphosphine | 121 | | |
| 36 | Hexadecacarbonyl hexarhodium $Rh_6(CO)_{16}$ | 36 | 14.0 | 81.5 |
| | Tricyclohexylphosphine | 168 | | |
| 37 | Hexadecacarbonyl hexarhodium $Rh_6(CO)_{16}$ | 36 | 11.0 | 85.2 |
| | Triethylphosphite | 249 | | |

EXAMPLE 38

After sweeping with nitrogen gas the interior of an autoclave which was equipped with a stirrer, had an internal volume of 200 ml and was made of stainless steel, 300 mg of rhodium chloride trihydrate and 240 mg of triethylamine were charged, followed by a further addition of 80 ml of ethanol as a reaction solvent. A 1:1 (by molar ratio) mixed gas of carbon monoxide and hydrogen was then charged under pressure and at room temperature into the autoclave until the internal pressure reached 80 kg/cm$^2$G. Thereafter, the internal temperature was raised to 100° C., at which the contents were continuously heated for 1 hour. The autoclave was then cooled to room temperature. After purging the gas, 15.6 g of vinyl chloride was added and a 1:1 (by molar ratio) mixed gas of carbon monoxide and hydrogen was charged again at room temperature until the internal pressure reached 80 kg/cm$^2$ G. The autoclave was then heated to 80° C., at which the contents were reacted for 30 minutes. After cooling the autoclave to room temperature, the unreacted mixed feed gas and reaction mixture were sampled and analyzed. The following productivity was obtained. Conversion of vinyl chloride: 4.3%. Selectivity toward 2-chloropropionaldehyde: 85.1%.

EXAMPLE 39

After sweeping with nitrogen gas the interior of an autoclave which was equipped with a stirrer, had an internal volume of 50 ml and was made of stainless steel, the autoclave was charged with 184 mg (0.2 milligram atom as Rh) of carbonylhydridotris(triphenylphosphine)rhodium and 218 mg (2.5 millimoles) of morpholine, followed by a further addition of 20 ml of a toluene solution which contained 3.75 g (60 millimoles) of vinyl chloride. A 1:2 (by molar ratio) mixed gas of carbon monoxide and hydrogen was then charged under pressure and at room temperature into the autoclave until the interior pressure increased to 75 kg/cm$^2$G. Thereafter, the autoclave was raised to 40° C. at which the contents were reacted for 120 minutes. After cooling the autoclave down to room temperature, the unreacted mixed feed gas was collected in a gas-sampling bag and the autoclave was then opened to take out the reaction mixture containing the catalyst, solvent and reaction product. The gas and the reaction mixture were both quantitatively analyzed by gas chromatography. As a result, the conversion of vinyl chloride and the yield of 2-chloropropionaldehyde were respectively found to be 19.9% and 10.9 millimoles (selectivity: 91.3% based on the converted vinyl chloride). It was also found that propionaldehyde occurred as a principal byproduct with a selectivity of 4.8%.

EXAMPLES 40–41

Reactions were effected in the same manner as in Example 39 except that the reaction temperature was changed to 50° C. and various bases were respectively used in lieu of morpholine. Results are summarized in Table 6.

TABLE 6

| Ex. | Base | Conversion of vinyl chloride (%) | Selectivity toward 2-chloropropionaldehyde (%) |
|---|---|---|---|
| 40 | N—Methylmorpholine | 14.4 | 90.1 |
| 41 | N—Ethylmorpholine | 13.8 | 89.8 |

EXAMPLE 42

After sweeping with nitrogen gas the interior of an autoclave which was equipped with a stirrer, had an internal volume of 100 ml and was made of stainless steel, the autoclave was charged with 184 mg (0.2 milligram atom as Rh) of carbonylhydridotris(triphenylphosphine)rhodium, 335 mg (5 millimoles) of imidazole and 15 ml of water, followed by a further addition of 20 ml of a toluene solution which contained 3.75 g (60 millimoles) of vinyl chloride. A 1:2 (by molar ratio) mixed gas of carbon monoxide and hydrogen was then charged under pressure and at room temperature into the autoclave until the interior pressure increased to 75 kg/cm$^2$G. Thereafter, the autoclave was raised to 40° C. at which the contents were reacted for 60 minutes. After cooling the autoclave down to room temperature, the unreacted mixed feed gas was collected in a gas-sampling bag and the autoclave was then opened to take out the reaction mixture containing the catalyst, solvent and reaction product. The gas and the reaction mixture were both quantitatively analyzed by gas chromatography. As a result, the conversion of vinyl chloride and the yield of 2-chloropropionaldehyde were respectively found to be 19.3% and 10.4 millimoles (selectivity:

90.1% based on the converted vinyl chloride). It was also found that propionaldehyde occurred as a principal byproduct with a selectivity of 4.9%.

EXAMPLES 43-53

Reactions were carried out for 90 minutes in the same manner as in Example 42 except that the temperature was changed to 50° C. and various bases were respectively used in place of imidazole. Results are summarized in Table 7.

TABLE 7

| Ex. | Base | Conversion of vinyl chloride (%) | Selectivity toward 2-chloropropionaldehyde (%) |
|---|---|---|---|
| 43 | Morpholine | 30.2 | 93.1 |
| 44 | N—Methylmorpholine | 28.7 | 92.6 |
| 45 | N—Ethylmorpholine | 26.2 | 91.3 |
| 46 | Pyridine | 2.1 | 84.2 |
| 47 | Picoline | 2.8 | 83.1 |
| 48 | 2,4-Lutidine | 4.2 | 86.5 |
| 49 | 4-Methylquinoline | 1.9 | 88.1 |
| 50 | N—Methylimidazole | 26.3 | 90.2 |
| 51 | 2-Undecylimidazole | 24.2 | 91.1 |
| 52 | Benzimidazole | 21.5 | 89.3 |
| 53 | 2-Methylbenzimidazole | 20.3 | 86.4 |

EXAMPLE 54

A reaction was carried out in the same manner as in Example 42 except that 0.1 ml of water was used instead of 15 ml of water. From analyses of the unreacted mixed feed gas and reaction mixture, the following productivity was obtained. Conversion of vinyl chloride: 16.6%. Selectivity towared 2-chloropropionaldehyde: 90.6%.

EXAMPLE 55

A reaction was carried out in the same manner as in Example 42 except that 40 ml of water was used instead of 15 ml of water. From analyses of the unreacted mixed feed gas and reaction mixture, the following productivity was obtained. Conversion of vinyl chloride: 17.2%. Selectivity toward 2-chloropropionaldehyde: 88.3%.

EXAMPLE 56

A reaction was carried out in the same manner as in Example 42 except that 50 ml of water was used instead of 15 ml of water and 10 ml of a toluene solution containing 1.2 g of vinyl chloride was used in place of 20 ml of the toluene solution containing 3.75 g of vinyl chloride. From analyses of the unreacted mixed feed gas and reaction mixture, the following productivity was obtained. Conversion of vinyl chloride: 16.1%. Selectivity toward 2-chloropropionaldehyde: 91.0%.

EXAMPLE 57

A reaction was carried out in the same manner as in Example 42 except that 10 g of vinyl chloride free of any solvent was used in place of 20 ml of the toluene solution containing 3.75 g of vinyl chloride. From analyses of the unreacted mixed feed gas and reaction mixture after the reaction, the following productivity was obtained. Conversion of vinyl chloride: 28.1%. Selectivity toward 2-chloropropionaldehyde: 87.1%.

EXAMPLE 58

Charged in an autoclave (withstandable maximum pressure: 150 kg/cm$^2$G, internal volume: 2 l, material: SUS 304) equipped with a stirrer were 7.37 g (8 mmol) of carbonylhydridotris(triphenylphosphine)rhodium [RhH(CO)(Ph$_3$P)$_3$], 10.9 g (160 mmol) of imidazole, 400 ml of toluene and 400 ml of water. The lid of the autoclave was closed and the interior air of the autoclave was swept off with nitrogen gas, and 200 g (3.2 mol) of vinyl chloride was charged into the autoclave. Thereafter, a 1:2 (by molar ratio) mixed gas of carbon monoxide and hydrogen was introduced under pressure into the autoclave until the internal pressure reached 100 kg/cm$^2$G. The autoclave was then immersed in a warm water bath of 62° C. After its internal temperature reached 60° C., the contents were reacted with stirring at the constant temperature for 30 minutes. During the reaction, the internal pressure of the autoclave tended to drop as the reaction proceeded. However, the internal pressure of the autoclave was maintained at 95-100 kg/cm$^2$G by intermittent supplementation of a 1:2 (by molar ratio) mixed gas of carbon monoxide and hydrogen. After the reaction, the pressure was released and the contents of the autoclave, namely, the reaction mixture was taken out. It was then transferred in a separating funnel, in which it was left over at rest so as to separate it into an upper layer, i.e., an organic layer (toluene layer) and a lower layer, i.e., a water layer. The water layer contained 120.3 g (1.3 mol) of 2-chloropropionaldehyde, the intended reaction product, and 10.8 g (159 mmol) of imidazole which was used as one of bases in the present invention. Besides, were also detected 7.9 g (136.2 mmol) of propionaldehyde as a byproduct and 143 mmol of chlorine ions. The water layer was distilled at 63° C. under reduced pressured (520 mmHg). The initial fraction of the distillation consisted principally of propionaldehyde. By throwing away the initial fraction, 123.2 g of 2-chloropropionaldehyde containing 10.2 wt. % of water was obtained. No other compounds were detected by gas chromatography in the thus-obtained 2-chloropropionaldehyde. In the aqueous still residue resulted from the distillation under reduced pressure, were detected a small amount of propionic acid in addition to 10.8 g of imidazole and 143 mmol of chlorine ions. The aqueous still residue was loaded on a glass column which was packed with 500 ml of a strongly-basic anion-exchange resin (Lewatit M500, trade name; product of Bayer AG) which had in advance been regenerated to its OH-active form, whereby chlorine ions and propionic acid were both removed and a purified aqueous solution containing 10.6 g of imidazole was recovered. As will be described later on, the imidazole-containing aqueous solution was concentrated to adjust its water content and was then provided for use in the next reaction, in which sufficient productivity was achieved.

Besides toluene, the triphenylphosphine containing complex of rhodium was also contained without any substantial loss of rhodium and triphenylphosphine in the organic layer. Furthermore, 113 mmol of 2-chloropropionaldehyde and a trace amount of imidazole were also dissolved in the organic layer. The organic layer was washed with 400 ml of water to reduce the content of 2-chloropropionaldehyde to 7.5 mmol. The thus-treated organic layer was charged back in the same 2 l autoclave, followed by a further addition of 410.9 g of an aqueous solution which had been prepared by adding a fresh supply of imidazole to the above-recovered aqueous imidazole solution and contained 10.9 g of imidazole. After closing the lid of the autoclave and sweeping the interior air with nitrogen gas, the reaction between vinyl chloride and carbon monoxide and hydrogen was conducted in the same manner as in the above-effected first reaction. The resultant reaction mixture was also treated in the same manner as the above-described treatment. As a result, 125.6 g of 2-chloropropionaldehyde containing 10.4 wt. % of water was obtained in the second reaction. Repeating the same procedure, the third, fourth, fifth and sixth reactions were conducted. 2-Chloropropionaldehyde, the water content of which was 10.4 wt. % on average, was obtained in amounts of 127.2 g, 122.8 g, 123.4 g and 124.1 g respectively.

EXAMPLE 59

While maintaining a reactor equipped with a stirrer constructed of blades arranged in four vertical levels and a warm-water jacket and made of SUS 316 (withstandable maximum pressure: 200 kg/cm$^2$G, inner diameter: 30 mm, height: 450 mm; actual volume: about 300 ml) at 70° C. and 90 kg/cm$^2$G, a rhodium catalyst solution (a toluene solution containing 20 mg atom of rhodium, 80 mmol of triphenylphosphine, 20.0 mmol of 2-chloropropionaldehyde and 23 mmol of imidazole, all per liter of the toluene solution), an aqueous imidazole solution (which contained 500 mmol of imidazole per liter), vinyl chloride and a 1:2 (by molar ratio) mixed gas of carbon monoxide and hydrogen were continuously fed through a feed pipe provided in a lower part of the reactor at flow velocities of 600 ml/hr., 600 ml/hr., 7.2 mol/hr. and 240 l/hr. respectively. At the same time, a reaction mixture containing a water layer and an organic layer as well as unreacted vinyl chloride, carbon monoxide and hydrogen were continuously delivered from the reactor to a gas-liquid separator operated at 25° C. and the same pressure as the reactor.

In the gas-liquid separator, a major portion of the unreacted vinyl chloride as well as the unreacted carbon monoxide and hydrogen were withdrawn through a gas discharge port provided in an upper part of the separator. They were then fed, via a pressure control valve, to an unreacted-gas reservoir which was maintained at atmospheric pressure. On the other hand, the reaction mixture was taken out of the gas-liquid separator through a liquid discharge port provided in a lower part of the separator. The reaction mixture was then delivered, via a liquid level control valve, to a static separation tank which was operated under atmospheric pressure, where the reaction mixture was separated into an upper layer, i.e., an organic layer (toluene layer) and a lower layer, i.e., a water layer. The organic layer was washed with water in the same amount to remove the majority of 2-chloropropionaldehyde contained therein. The thus-obtained organic layer was substantially of the same composition as the aforementioned rhodium catalyst solution. For its reutilization, it was mixed with the rhodium catalyst solution which was to be fed to the reactor. On the other hand, the water layer was stored over 4 hours and was then intermittently fed in about 3,300 ml portions to a reduced-pressure batch distillation apparatus which was operated at a pressure of 500 mmHg, a bottom temperature of 70° C. and a top temperature of 60° C., thereby subjecting the water layer to distillation. In each distillation, the initial fraction of about 50 ml was thrown away. Thereafter, the fraction which boiled out at an overhead temperature of 60° C. was collected in its entirety. After each distillation, 2400 g of an aqueous solution containing 1180 mmol of imidazole on average was obtained as a still residue of the reduced-pressure distillation. In the aqueous solution, about 460 mmol of chlorine ions and 3.7 g of propionic acid were contained as impurities. The still residue was purified with a strongly basic anion-exchange resin in the same manner as that described in Example 58, whereby about 600 ml of an aqueous solution containing 295 mmol of imidazole was obtained on average per hour. It was also mixed, for its reutilization, with the aqueous imidazole solution which was to be fed to the reactor.

In the above manner, a continuous operation was conducted over 30 hours. The distillate from the reduced-pressure distillation apparatus was 2-chloropropionaldehyde which contained 10.2 wt. % of water on average. Its yield per hour was leveled off within the range of ±5% or so from about the 8$^{th}$ hour after the initiation of the operation and thereafter remained at substantially the same level until the 30$^{th}$ hour. During the four-hour period from the 24$^{th}$ hour to the 28$^{th}$ hour after the initiation of the reaction, 214 g of 2-chloropropionaldehyde containing 10.1 wt. % of water was obtained on average per hour.

REFERENTIAL EXAMPLE 1

The procedure of Example 1 was repeated except that 36 mg of hexadecacarbonyl hexarhodium was used in place of carbonylhydridotris(triphenylphosphine)rhodium and the reaction was effected in the absence of imidazole. No occurrence of 2-chloropropionaldehyde was observed in the autoclave after the reaction.

REFERENTIAL EXAMPLE 2

The procedure of Referential Example 1 was repeated except that 226 mg of octacarbonyl dicobalt was used in place of hexadecacarbonyl hexarhodium. Occurrence of 2-chloropropionaldehyde was observed but only in a trace amount.

What is claimed is:

1. A process for preparing 2-chloropropionaldehyde, which comprises reacting vinyl chloride, carbon monoxide and hydrogen in the presence of a rhodium compound and a base, said base composed in combination of:

at least one compound represented by the following general formula:

wherein P means a phosphorus atom, and $R^1$, $R_2$ and $R^3$ denote individually an alkyl, aryl, cycloalkyl, alkoxy, aryloxy or cycloalkoxy group; and at least one nitrogen-containing compound the pKa of which is in the range of 4-10; and said reaction being effected at a temperature in the range of 20°-100° C.

2. A process as claimed in claim 1 wherein the nitrogen-containing compound, the pKa of which is in the range of 4-10, is a nitrogen compound selected from pyridine compounds, quinoline compounds, imidazole compounds and morpholine compounds and having a pKa in the range of 4-10.

3. A process as claimed in claim 1, wherein the reaction is carried out in the presence of water.

4. A process as claimed in claim 6, wherein the water is present at a weight ratio of 0.001-100 relative to the vinyl chloride.

5. A process as claimed in claim 1, wherein the rhodium compound is free of any halogen.

6. A process for preparing 2-chloropropionaldehyde, which comprises:
   (a) reacting, at a temperature in the range of 20°–100° C., vinyl chloride, carbon monoxide and hydrogen in the presence of a rhodium compound, a base which is composed in combination of:
   at least one compound represented by the following general formula:

$P(R^1R^2R^3)$ wherein P means a phosphorus atom, and $R^1$, $R^2$ and $R^3$ denote individually an alkyl, aryl, cycloalkyl, alkoxy, aryloxy or cycloalkoxy group, and
   at least one nitrogen-containing compound the pKa of which is in the range of 4–10, an organic solvent which is insoluble or hardly soluble in water, and water;
   (b) fractionating the thus-obtained reaction mixture into a water layer and an organic layer;
   (c) recycling the organic layer to the reaction system for its reutilization; and
   (d) obtaining the reaction product, 2-chloropropionaldehyde, from the water layer by a method known per se in the art such as distillation or extraction.

7. A process as claimed in claim 6, wherein the organic layer is recycled for its reutilization after extracting the major part of remaining 2-chloropropionaldehyde from the organic layer with water.

8. A process as claimed in claim 7, wherein the nitrogen-containing compound, the pKa of which is in the range of 4–10, is a nitrogen-containing compound selected from pyridine compounds, quinoline compounds, imidazole compounds and morpholine compounds and having a pKa in the range of 4–10.

9. A process as claimed in claim 6, wherein the water is present at a weight ratio of 0.001–100 relative to the vinyl chloride.

10. A process as claimed in claim 6, wherein the rhodium compound is free of any halogen.

11. A process as claimed in claim 1, wherein the reaction is effected at a pressure in the range of 10–200 kg/cm²G.

12. A process as claimed in claim 6 wherein the reaction is effected at a pressure in the range of 10–200 kg/cm²G.

* * * * *